Figure 1:
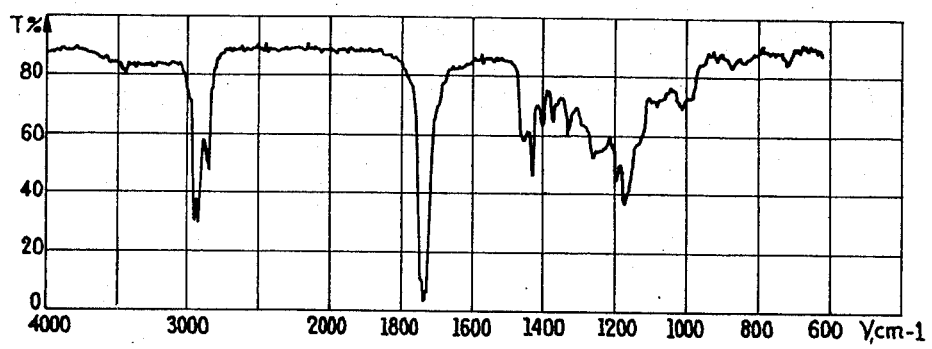

United States Patent [19]
Teisseire et al.

[11] 3,978,108
[45] Aug. 31, 1976

[54] CIS METHYL DIHYDROJASMONATE

[75] Inventors: Paul Jose Teisseire, Grasse; Marcel Plattier, Antibes, both of France

[73] Assignee: Societe Anonyme des Establissements Roure-Bertrand Fils & Justin Dupont, Paris, France

[22] Filed: Dec. 17, 1971

[21] Appl. No.: 209,239

[30] Foreign Application Priority Data

Dec. 23, 1970 France ............................. 70.46407

[52] U.S. Cl. ............................. 260/468 K; 252/522; 260/340.9
[51] Int. Cl.² ........................................ C07C 69/74
[58] Field of Search ..... 260/468 K, 514 K, 514 CA; 252/522

[56] References Cited
UNITED STATES PATENTS

| | | | |
|---|---|---|---|
| 3,158,644 | 11/1964 | Demole et al. | 260/468 |
| 3,754,016 | 8/1973 | Oberhansli | 260/468 |

FOREIGN PATENTS OR APPLICATIONS

| | | | |
|---|---|---|---|
| 2,008,878 | 9/1970 | Germany | 260/468 |
| 1,206,981 | 9/1970 | United Kingdom | 260/660 |

OTHER PUBLICATIONS

House, Modern Synthetic Reactions, pp. 19, 20, 26–28, 615, (1972).

*Primary Examiner*—Robert Gerstl
*Attorney, Agent, or Firm*—Wallenstein, Spangenberg, Hattis & Strampel

[57] ABSTRACT

Methyl dihydrojasmonate containing a major proportion of cis methyl dihydrojasmonate. The NMR spectrum of cis methyl dihydrojasmonate is illustrated in the attached drawings.

Cis methyl dihydrojasmonate displays olfactory properties superior to those of the trans isomer making it very useful as an odoriferous agent. In order to prepare methyl dihydrojasmonate containing a major proportion and preferably at least 90% of cis isomer, methyl (2-pentyl-3-keto-cyclopenten-1-yl)-acetate is catalytically hydrogenated in the presence of an aluminium derivative.

2 Claims, 8 Drawing Figures

CIS METHYL DIHYDROJASMONATE

The present invention relates to methyl dihydrojasmonate, a compound with a jasmine-like odour which can be used in the preparation of perfumed compositions.

The preparation of methyl dihydrojasmonate, the chemical name of which is methyl (2-pentyl-3-keto-cyclopentyl)-acetate, is described in French Pat. No. 1,280,432 as well as in U.S. Pat. No. 3,158,644. While methyl dihydrojasmonate is capable of existing in both the trans and cis forms, and is so generally indicated, for instance, in said U.S. patent, the face is that the cis form has not heretofore been isolated nor characterized. Furthermore, the process disclosed in said patents, production of either 100% of the trans isomer or possibly a very small percentage at best of the cis isomer intermingled with the essentially overwhelming content of the trans isomer, the latter constituting no less than about 95% by weight, perhaps more, of the methyl dihydrojasmonate. These two forms can be represented, in accordance with the usual conventions, by formulae I and II respectively.

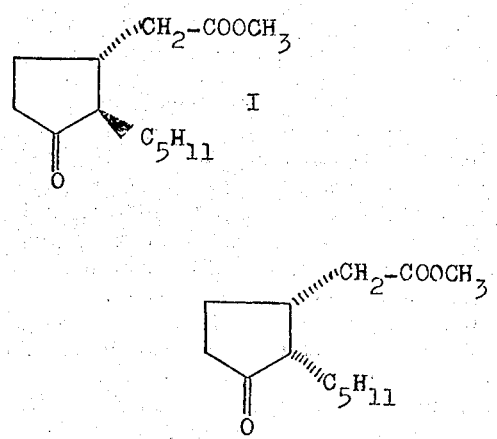

Thus by the term "methyl dihydrojasmonate" as used herein without any isomer designation, we mean a mixture of the cis and trans isomer thereof.

A process has now been found which enables the production of methyl dihydrojasmonate containing a major proportion, that is, more than 50% by weight, of the cis isomer. The process of this invention has proved to be capable of giving a methyl dihydrojasmonate containing upwards of 90% of the cis isomer.

It has furthermore surprisingly been found that cis methyl dihydrojasmonate and also methyl dihydrojasmonate containing a major proportion of the cis isomer is distinguished from the earlier trans product both by its olfactory characteristics and in that the physicochemical properties of the cis isomer differ from those of the trans isomer.

This invention thus relates to a process for the preparation of cis methyl dihydrojasmonate or methyl dihydrojasmonate containing a major proportion of the cis isomer and perfumed compositions containing said compound or mixture of isomers.

The process according to the present invention is thus a process for the preparation of methyl dihydrojasmonate containing a major proportion of cis methyl dihydrojasmonate, which comprises catalytically hydrogenating methyl(2-pentyl-3-keto-cyclopenten-1-yl)-acetate in the presence of an aluminium derivative.

The methyl dihydrojasmonate produced most advantageously has a cis isomer content of at least 90%.

Also according to the present invention there is provided methyl dihydrojasmonate containing a major proportion, especially at least 90%, of cis methyl dihydrojasmonate.

Further, according to the present invention there is provided substantially pure cis methyl dihydrojasmonate having in its infrared spectrum single bands at 1010 $cm^{-1}$ and 1250 $cm^{-1}$, a small band at 1095 $cm^{-1}$ and a medium band at 1310 $cm^{-1}$ and, in its NMR spectrum, a multiplet centered at 2.72 p.p.m. corresponding to the proton situated $\alpha$ to the carbonyl group.

Methyl (2-pentyl-3-keto-cyclopenten-1-yl)-acetate has the formula III

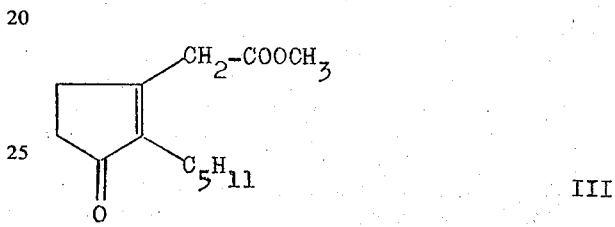

For the sake of brevity and by analogy with methyl dihydrojasmonate, it will be hereinafter designated methyl dehydrodihydrojasmonate. Methyl dehydrodihydrojasmonate is a known compound which has been described in Belgian Pat. No. 745937 and in the Perfumer and Essential Oil Record 1969 p. 267 by K. Sisido, S. Kurozumi and K. Utimoto.

Any organic derivative of aluminium may be used in the hydrogenation process in accordance with the invention, it being preferred to use an aluminium alcoholate since they are readily available and easy to use in the reaction. The aluminium alcoholate can be added to the reaction mixture as such or may be prepared in situ, for example by using a mixture of an alkylaluminium and an alcohol.

The hydrogenation can be effected in a homogeneous reaction medium by the addition of a sufficient quantity of a third solvent component such as an alcohol or an ester. This is, however, not essential since better yields appear to be obtained when the reaction is effected in a heterogenous reaction medium, for example in the presence of an amount of a third solvent component which is not sufficient to render the reaction medium homogeneous. In this case, a dispersant such as aluminium stearate is preferably added to the reaction mixture.

When employing an aluminium alcoholate, it is preferred to use aluminium methylate in order to avoid a trans-esterification reaction occurring between the alcohol of the alcoholate and the methyl group of methyl dehydrodihydrojasmonate or of its hydrogenated derivative. Whilst this trans-esterification reduces the yield it does not, however, affect the percentage of the cis isomer obtained. It is, however, preferable that, when an alcohol is used as the third solvent component, it is methanol.

The quantity of aluminium derivative used is not critical. However, it is preferred to use about 1 gram atom per mol of compound III.

The catalytic hydrogenation is advantageously carried out under a pressure of from 3 to 10 kg/cm² and at a temperature of from 30° to 80°C. Catalysts which may be used for the hydrogenation include such conventional catalysts as palladium or rhodium deposited in an amount of 5 or 10% by weight on carbon, platinum, platinum oxide or Raney-nickel.

The catalyst is conveniently used in an amount of from 1 to 10% by weight, based on the amount of the compound of formula III.

Because of its remarkable olfactory properties, cis methyl dihydrojasmonate and methyl dihydrojasmonate containing a major proportion of the cis isomer are valuable ingredients for perfumes and perfumed compositions. They have good stability during storage. Moreover, the stability of cis-methyl dihydrojasmonate appears to be increased when it is in admixture with the constituents conventionally employed in the preparation of perfumed compositions such as perfumes and toilet waters.

The following Examples demonstrate in detail the differences between the properties of cis and trans methyl dihydrojasmonate. In this connection, it should be emphasized that this distinction is in certain respects a delicate one. Some of the physicochemical and spectral characteristics of the two isomers are, in fact, adjacent to one another. However, the spectra have certain characteristic differences as described in more detail below. Furthermore, olfactory investigation and gas-phase chromatographic investigation permit the unambiguous characterization of the two isomers. Thus, the odour of the cis isomer is in particular devoid of a fatty note, more floral than that of the trans isomer and much more jasmine-like than the latter in the course of evaporation.

To a certain extent the gas-phase chromatography results given below require qualification. Gas-phase chromatographic analysis involves the use of elevated temperatures. At such elevated temperatures a partial epimerisation of the cis isomer into the trans isomer occurs, since the cis isomer is thermodynamically less stable than the trans isomer. This has the effect that the quantitative gas-chromatographic analysis of the two isomers gives an inaccurate result. The proportion of cis isomer thus found by the latter method in the product in accordance with the invention is of necessity underestimated. It is considered that the product obtained by the process of this invention presents a higher content of cis isomer which may in some cases approach, even if it does not reach, 100%, as the nuclear magnetic resonance spectrum suggests.

Further characterisation of the cis and trans isomers of methyl dihydrojasmonate was effected by way of the preparation and characterisation of the dioxolane derivatives having the formula

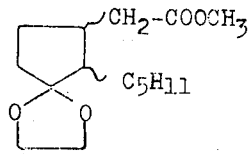

IV

The dioxolane derivative, that is to say a mixture of the dioxolanes of cis and trans methyl dihydrojasmonate and also the pure dioxolanes of the two individual isomers, are novel compounds. They are furthermore valuable not only for the characterization of the cis and trans isomers of methyl dihydrojasmonate, but are also useful intermediates for the preparation of other derivatives of methyl dihydrojasmonate, and accordingly constitute a further feature of this invention.

The dioxolane derivatives furthermore possess an interesting floral odour and are hence useful for the preparation of odoriferous compositions. They may be incorporated into perfumes, toilet waters, cosmetics and other perfumed commercial products such as washing powders and liquids, aerosols and soaps. The amounts in which the dioxolanes of the invention may be used in the preparation of odoriferous products varies widely depending on the end product. Thus, for example, in perfumes they may conveniently be used in an amount of from 0.5 to 10% by weight.

The invention will now be further illustrated with reference to the following Examples.

EXAMPLE 1

120 g of aluminium methylate (1 mol), 700 ml of anhydrous methanol and 224 g of methyl dehydrodihydrojasmonate (1 mol) were introduced into a 2-liter autoclave. The autoclave was purged with a current of dry nitrogen and 20 g of 5% palladium-on-carbon were introduced. The autoclave was closed and the temperature of the reaction medium raised to 40°C. Agitation was commenced and the temperature was maintained at 40°C for 1 hour. Hydrogen was subsequently introduced under a pressure of 7 kg/cm². Hydrogenation then commenced and was continued for 3 hours during which time the temperature of the reaction medium was maintained between 40° and 60°C. After the end of the hydrogenation, the autoclave was once more purged with a current of nitrogen. Three liters of a 10% aqueous solution of acetic acid were then added and the resulting slurry was suction-filtered in order to separate the catalyst. The heterogeneous filtrate and the catalyst were extracted with petroleum ether. The washed and dried petroleum ether solutions were then distilled. There were thus obtained 220 g of crude product which were redistilled under a pressure of 0.15 mm of mercury to give 215 g of distillate, or a yield of about 95%.

$B_{0.15} = 95° - 98°C \quad n_D^{15} = 1.4638$

The chromatographic analysis of this distillate was effected under the following conditions. A stainless steel column 4 meters long and 3.175 mm in diameter was emloyed. This column was filled with 3% of "O V 1" as stationary phase on "Chromosorb G" of granule size 0.149 – 0.177 mm as support. ("O V 1" is a completely methylated silicone of molecular weight included between 3 and 4 × 10⁶). The carrier gas was helium, its flow was 17 ml/mm. The temperature of the column was 150°C, that of the injector 180°C.

Under these conditions, the above distillate furnished two peaks, quantitative working of which indicated a content of about 90% of cis methyl dihydrojasmonate.

The retention times were as follows:

| | |
|---|---|
| peak No. 1 trans methyl dihydrojasmonate: | 57.15 min. |
| peak No. 2 cis methyl dihydrojasmonate: | 64.55 min. |

The front of the trans methyl dihydrojasmonate peak was perfectly symmetrical, but an important "tail" was observed between this peak and the following peak which was that of cis methyl dihydrojasmonate, which was present due to the cis/trans isomerization which took place actually during the course of the chromatography. As has been discussed above, the isomerization was a partial epimerisation of the cis derivative into the thermodynamically more stable trans derivative.

A total epimerisation of the cis isomer into the trans isomer was carried out by heating in an alkaline medium, for example by refluxing the cis isomer for two hours in a normal methanolic solution of sodium methylate. This process enabled the separate preparation of the cis and trans isomers and a comparison of their properties. Further characterization of the cis and trans isomers may be effected by preparing the dioxolane derivatives thereof.

The dioxolane derivatives can be prepared as follows:

135.6 g of the cis or trans isomer (0.6 mol) were mixed with 187 g of mixed ethylene glycol methyl orthoformate (1.8 mol). 0.3 ml of boron trifluoride etherate were added to the solution obtained; the solution immediately took on a violet colouration. It was left for about 20 hours at the ordinary temperature with light stirring. 24 g of powdered sodium carbonate were subsequently added thereto, the mixture was stirred for 15 minutes and subsequently slurried in 600 ml of a 9% aqueous solution of sodium bicarbonate. It was extracted three times with 200 ml of petroleum ether. The petroleum ether solutions were washed twice with 200 ml of water.

By distillation of the petroleum ether, there were obtained 165 g of crude product which was rectified under a pressure of 0.2 mm of mercury. There were thus obtained 160 g of cis or trans dioxolane, which represents a practically quantitative yield. The physical properties of these derivatives were:

cis-dioxolane $B_{0.2} = 113° - 114°C$ $n_D^{15} = 1.4670$ trans-dioxolane $B_{0.2} = 101° - 102°C$ $n_D^{15} = 1.4650$ The chromatographic analysis of the dioxolanes of cis and trans methyl dihydrojasmonate, compared with that of the dihydrojasmonates themselves, emphasises that in this case there is no epimerisation of the cis derivative, the peaks obtained being perfectly symmetrical for the two varieties. This analysis was effected under the following conditions:

A stainless steel column 2 meters long and 10 mm in diameter was used. This column was filled with 20% "Carbowax 20 M" as the stationary phase on "Celite J J's" having a particle size of 0.250–0.420 mm as the support. The carrier gas was helium and its flow rate was 250 ml/min. The temperature of the column was 170°C and that of the injector 190°C.

Under these conditions, the retention times were as follows:

Dioxane derivative of trans methyl dihydrojasmonate: 2 h 17 min.

Dioxane derivative of cis methyl dihydrojasmonate: 2 h 40 min.

In addition, both the cis and trans isomers of methyl dihydrojasmonate and also the corresponding dioxolane derivatives were submitted to spectral analyses (infrared spectrum and N.M.R. spectrum).

Figure 2:
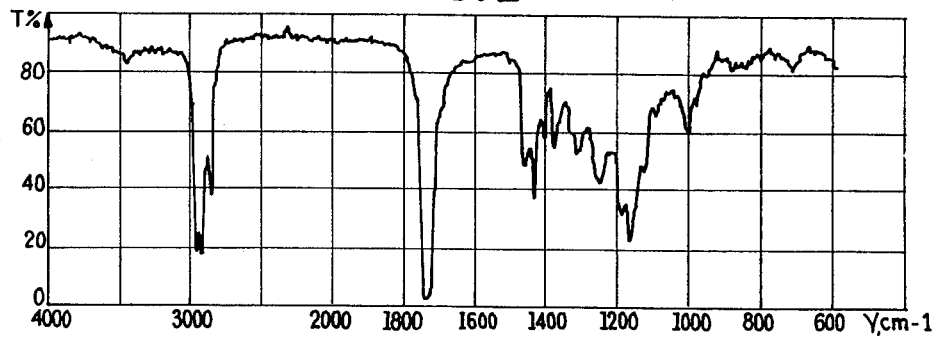
Figure 3:
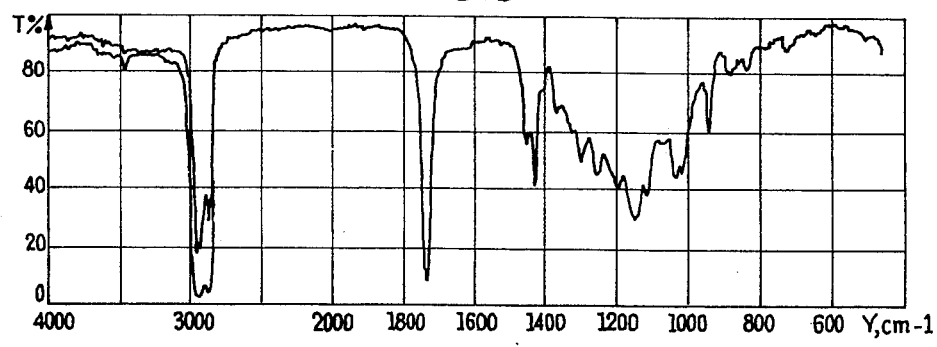
Figure 4:
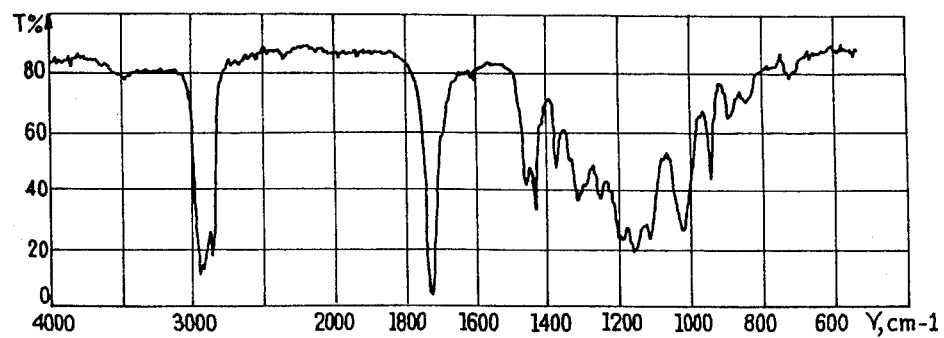
Figure 5:
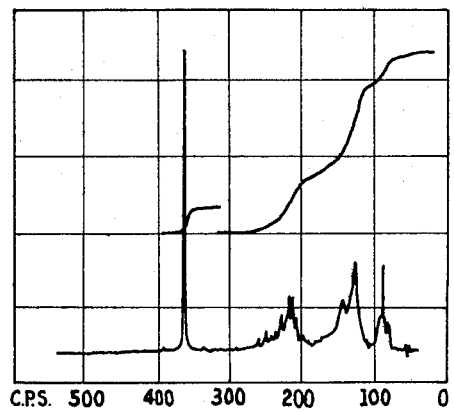
Figure 6:
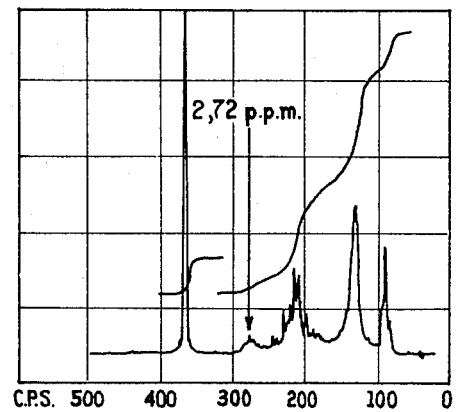
Figure 7:
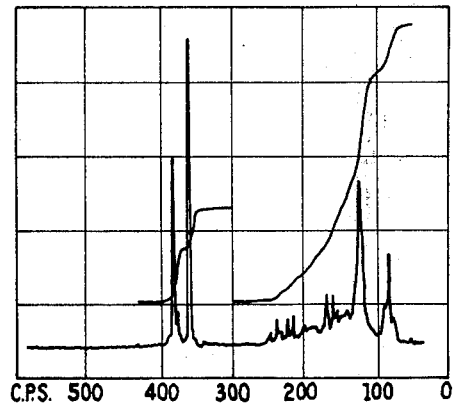
Figure 8:
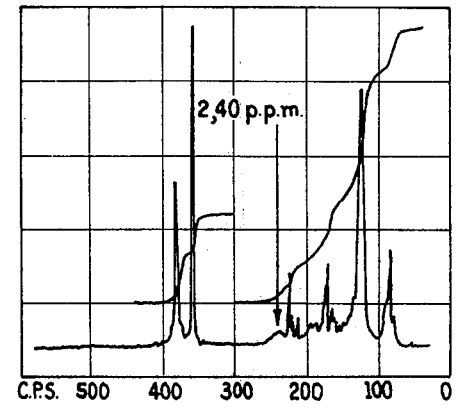

The resulting spectra are shown in FIGS. 1 to 8 of the attached drawings.

FIGS. 1 to 4, in which the frequency in $cm^{-1}$ has been plotted on the abscissae and the degree of transmission T% on the ordinates show the infrared spectra of the trans isomer, the cis isomer, the trans dioxolane and the cis dioxolane respectively.

FIGS. 5 to 8 show the N.M.R. spectra of the trans isomer, the cis isomer, the trans dioxolane and the cis dioxolane respectively. These spectra were recorded on a Varian HA100 apparatus (frequency 100 megaherz), the products being in solution in carbon tetrachloride. Tetramethylsilcane (TMB) was used as the internal standard. On the abcissae are plotted the frequencies in cycles per second (c.p.s.) or herz.

The principal differences between the spectra of the cis and trans methyl dihydrojasmonates as shown by the accompanying drawings are summarized below.

| cis Methyl dihydrojasmonate | trans Methyl dihydrojasmonate |
|---|---|
| 1) IR spectra (FIG. 2) | (FIG. 1) |
| Single band at 1010 $cm^{-1}$ | Double band with maxima at 985 and 1025 $cm^{-1}$ |
| Single band at 1250 $cm^{-1}$ | Double band (large with maxima at 1235 and 1255 $cm^{-1}$) |
| Small band at 1095 $cm^{-1}$ | No band for these |
| Moderate band at 1310 $cm^{-1}$ | wavelengths |
| 2) NMR spectra (FIG. 6) | (FIG. 5) |
| Triplet centred at 0.88 p.p.m. (3H) ($CH_3$ in the side-chain) | Triplet centred at 0.88 p.p.m. (3H) ($CH_3$ in the side-chain) |
| Large peak centred at 1.30 p.p.m. | Two large peaks centred at 1.27 and 1.46 p.p.m. |
| Very complex cluster extending from 1.6 to 2.54 p.p.m. | Very complex cluster extending from 1.7 to 2.63 p.p.m. |
| Complex multiplet centred at 2.72 p.p.m. 1 H | Nothing |
| Fine singlet at 3.6 p.p.m.(3H) ($CH_3$ of the methyl ester grouping) | Fine singlet at 3.6 p.p.m.(3H) ($CH_3$ of the methyl ester group) |

The complex multiplet centred at 2.72 p.p.m., corresponding to a proton, is characteristic of the cis derivative. Moreover, this multiplet also occurs in the spectrum of the corresponding dioxolane, in which it is then centred at 2.40 p.p.m. It is due to the proton situated $\alpha$ to the carbonyl grouping. It must be noted that this proton, being coupled with numerous other protons, is not analysable to the first order. This analysis is based on the fact that this proton is strongly shielded by one of the C—O bonds of the dioxolane group, which leads to an important displacement (2.72–2.40 = 0.32 ppm) from the initial field of this proton to higher fields. The precise integration of the multiplet corresponds to one proton, which is indicative of a pure product.

EXAMPLE 2

102 g of distilled aluminium isopropylate (0.5 mol), 600 ml of anhydrous ethyl acetate and 112 g of methyl dehydrodihydrojasmonate were introduced into a two-liter autoclave. The general procedure as set out in Example 1 was then followed and 10 g of 5% palladium-on-carbon were added. The hydrogenation was effected under an initial pressure of 5 kg/cm² while maintaining the temperature between 50° and 60°C for three hours. The working-up operation was also carried out as described in Example 1. There were thus obtained 88 g of distilled product ($B_{0.15} = 96°-99°C$), which represents a yield of about 78%. The lower yield relative to that obtained in Example 1 arose from the formation of isopropyl ester resulting from the exchange reaction between methanol and isopropanol.

The proportion of the methyl dihydrojasmonate in the product obtained, determined by gas chromatography, was of the same order as in Example 1.

EXAMPLE 3

430 ml of anhydrous methanol and 5 g of aluminium stearate were introduced into a two-liter flask, 108.9 g of triisobutylaluminium (0.55 mol) were subsequently slowly added while maintaining the temperature between 20° and 25°C by means of an external cooling bath. The reaction medium was subsequently refluxed for 1 hour and then cooled. 112 g of methyl dehydrodihydrojasmonate (0.5 mol) were then added and the resulting mixture was stirred at ambient temperature for 1 hour. The reaction medium was then transferred into an autoclave and the flask rinsed with 40 ml of methanol. After the usual purges, 10 g of 5% palladium-on-carbon were added. The hydrogenation was effected under a pressure of 10 kg/cm$^2$ for 2 hours.

The working-up operation was carried out as described in Example 1. There were thus obtained 110 g of distilled methyl dihydrojasmonate which represents a practically theoretical yield. Chromatographic investigation of the product, effected under the conditions given in Example 1, indicated a cis methyl dihydrojasmonate content of greater than 90%.

EXAMPLE 4

225 ml of anhydrous methanol and 5 g of aluminium stearate were introduced into a two-liter flask and 108.9 g of triisobutylaluminium (0.55 mol) were added thereto. The resulting mixture was refluxed for one hour, cooled and a solution of 112 g of methyl dehydrodihydrojasmonate (0.5 mol) in 130 ml of anhydrous hexane was added with stirring. The resulting heterogeneous reaction medium mass thus obtained was than transferred into an autoclave, hydrogenated and worked up as described in Example 3. The results obtained were similar to those of Example 3, the proportion of cis methyl dihydrojasmonate, determined by gas chromatography, being slightly better.

The invention is further illustrated by two examples of concentrates incorporating cis methyl dihydrojasmonate given below.

| Concentrate A | |
|---|---|
| Essence of bergamotte zest | 300 |
| Essence of lemon zest | 120 |
| Essence of lavander Laragne 40% | 20 |
| Essence of vervain, Grasse | 20 |
| Essence of geranium Bourbon | 20 |
| Essence of petit-grain, American | 20 |
| Essence of clary [Salvia sclarea], Grasse | 30 |
| Essence of lavandin super | 40 |
| Essence of neroli | 5 |
| Linalyl acetate | 90 |
| Linalol | 160 |
| Oak moss, absolute | 25 |
| Essence of vetiver Bourbon | 30 |
| Essence of patchouly | 20 |
| Couminaldehyde | 20 |
| Musk ketone | 40 |
| cis Methyl dihydrojasmonate | 40 |
| | 1.000 |
| Concentrate B | |
| Essence of lemon zest extra | 60 |
| Essence of bergamotte zest | 100 |
| Essence of ylang ylang premiere | 30 |
| Essence of geranium Bourbon | 20 |
| Phenylacetaldehyde 50% | 20 |
| Hydroxydihydrocitronellal | 40 |
| Geranyl acetate | 60 |
| Hexylcinnamaldehyde | 40 |
| $C_{10}$ aldehyde 10% in ethyl phthalate (EP) | 10 |
| $C_{12}$ aldehyde 10% in EP | 10 |
| $C_{14}$ aldehyde 10% in EP | 10 |
| Ananolide 1% in EP | 30 |
| Phenylethyl alcohol | 30 |
| Jasmine absolute | 50 |
| Essence of rose | 60 |
| Rose, absolute | 20 |
| Oak moss, absolute | 20 |
| γ-Methylionone | 90 |
| Vetiveryl acetate | 110 |
| Essence of sandal, Mysore | 20 |
| Coumarin | 40 |
| Musk ketone | 20 |
| Cyclopentadecanolide | 30 |
| cis Methyl dihydrojasmonate | 80 |
| | 1.000 |

Both these concentrates A and B when made up into alcoholic solution to the extent of 4 to 5% or 15 to 16% gave respectively toilet waters and perfumes with excellent olfactory properties.

We claim:

1. Substantially pure cis methyl dihydrojasmonate having in its infrared spectrum single bands at 1010 cm$^{-1}$ and 1250 cm$^{-1}$, a small band at 1095 cm$^{-1}$ and a medium band at 1310 cm$^{-1}$ and, in its NMR spectrum, a multiplet centered at 2.72 p.p.m. corresponding to the proton situated α to the carbonyl group, and being substantially free from trans methyl dihydrojasmonate.

2. A methyl dihydrojasmonate composition in which cis methyl dihydrojasmonate constitutes at least 90% by weight of the composition.

* * * * *